United States Patent [19]

O'Neal

[11] 4,297,126
[45] Oct. 27, 1981

[54] IMIDAZOLINYL BENZAMIDES AS PLANT GROWTH REGULANTS

[75] Inventor: Thomas D. O'Neal, Princeton, N.J.

[73] Assignee: American Cyanamid Co., Stamford, Conn.

[21] Appl. No.: 103,898

[22] Filed: Dec. 17, 1979

Related U.S. Application Data

[62] Division of Ser. No. 868,090, Jan. 9, 1978, Pat. No. 4,201,565.

[51] Int. Cl.³ .............................................A01N 43/50
[52] U.S. Cl. ........................................... 71/78; 71/92
[58] Field of Search ...................................... 71/78, 92

[56] References Cited

U.S. PATENT DOCUMENTS

| | | | |
|---|---|---|---|
| 3,873,297 | 3/1975 | Kupelian | 71/78 |
| 4,069,035 | 1/1978 | Johnson | 71/78 |
| 4,093,441 | 6/1978 | Ashkar | 71/92 |
| 4,122,275 | 10/1978 | Los | 71/92 |
| 4,124,369 | 11/1978 | Kramer et al. | 71/78 |

Primary Examiner—Glennon H. Hollrah
Attorney, Agent, or Firm—H. G. Jackson

[57] ABSTRACT

This invention relates to a method for regulating the growth of crop plants by applying to the foliage, roots, stems, seeds or to soil in which the crop plants are grown, an effective plant growth regulating amount of an imidazolinyl benzamide having the structure:

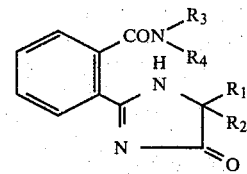

wherein $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl; and when $R_1$ and $R_2$ are taken together with the carbon to which they are attached they may form cycloalkyl $C_3$–$C_6$ optionally substituted with methyl; $R_3$ and $R_4$ each individually represent hydrogen, alkyl $C_1$–$C_4$, alkenyl $C_3$–$C_5$, alkynyl $C_3$–$C_5$, or benzyl; and when $R_1$ and $R_2$ represent different substituents, the optical isomers thereof.

2 Claims, No Drawings

IMIDAZOLINYL BENZAMIDES AS PLANT GROWTH REGULANTS

This is a division of application Ser. No. 868,090, filed Jan. 9, 1978 now U.S. Pat. No. 4,201,565 (1980).

DETAILED DESCRIPTION OF THE INVENTION

This invention relates to a method for regulating the growth of graminaceous crops and bean-producing legumes, by applying to the foliage, roots, stems, seeds, or to soil in which said crop plants are grown, an effective plant growth regulating amount of an imidazolinyl benzamide having the structure:

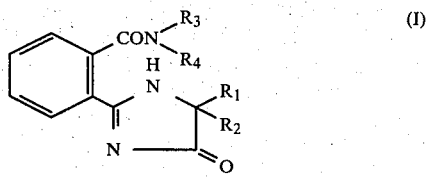

wherein $R_1$ is alkyl $C_1$–$C_4$; $R_2$ is alkyl $C_1$–$C_6$, cycloalkyl $C_3$–$C_6$, alkenyl $C_2$–$C_4$, phenyl, halophenyl or benzyl; and when $R_1$ and $R_2$ are taken together with the carbon to which they are attached they may form cycloalkyl $C_3$–$C_6$ optionally substituted with methyl; $R_3$ and $R_4$ each individually represent hydrogen, alkyl $C_1$–$C_4$, alkenyl $C_3$–$C_5$, alkynyl $C_3$–$C_5$, or benzyl; and when $R_1$ and $R_2$ represent different substituents, the optical isomers thereof.

The compounds useful herein are disclosed and claimed in coassigned U.S. Ser. No. 822,459, filed Aug. 8, 1977, in the name of Marinus Los.

The invention also relates to a method for inhibiting axillary growth on topped tobacco plants and woody plant species such as coffee trees by applying a bud growth inhibiting amount of a formula (I) imidazolinyl benzamide to the foliage and/or to the soil at the base of the stems of topped tobacco plants or to the trunks of said coffee trees.

Preferred compounds for the above-described utilities have the structure of formula I above, wherein $R_1$ is methyl; $R_2$ is alkyl $C_1$–$C_3$ (preferably isopropyl), or when $R_1$ and $R_2$ are taken together with the carbon to which they are attached they may represent cyclohexyl; $R_3$ and $R_4$ each individually represent hydrogen, alkyl $C_1$–$C_3$; and when $R_1$ and $R_2$ are different, the optical isomers thereof.

In accordance with the present invention, the plant growth regulating effects of formula I imidazolinyl benzamides applied to graminaceous crops, such as barley, oats, wheat, rice and corn, and to bean-producing legumes, such as snapbeans, lima beans, soybean and green beans, are generally characterized by a reduction in the relative stem growth of such crops. The treated crop plants are generally shorter and stockier than untreated plants and are less susceptible to lodging when subjected to atmospheric disturbances, such as wind and rain.

In practice, it is generally found that application of about 0.03 kg to 3.36 kg per hectare, and preferably 0.03 kg to 1.12 kg per hectare, of the active formula I imidazolinyl benzamide to the foliage, stems, roots, seeds, or to soil in which the crops are grown, provides the desirable reduction of relative stem growth (dwarfing) of graminaceous crops and bean-producing legumes.

In tobacco farming, maturation of the crop for harvesting is nitrated by removal of the apical flower growth of the tobacco plant in a process known as "topping." This process facilitates the development of large leaves which form the commercial crop. Their development, however, is offset by the enhanced development of laterial (axillary) buds. The laterial growth (called "sucker growth") again reduces the nutrient supply available for large leaf development. Thus, it is essential to control sucker growth on the tobacco plants if optimal production of marketable leaves is to be achieved.

It has also been found that about 4 mg to 150 mg of the formula I imidazolinyl benzamide applied to the foliage and stems or to soil at the base of the stems of topped tobacco plants will inhibit axillary growth on said plants. Similarly, application of the formula I imidazolinyl benzamide to the trunks of coffee trees, at the rate of about 500 mg to 3000 mg per tree, inhibits bud growth and sucker development on said coffee trees.

For use in accordance with the present invention, the formula I imidazolinyl benzamides are generally formulated as wettable powders, flowable liquids, emulsifiable concentrates or granular formulations. The wettable powders, flowable liquids and emulsifiable concentrates are then dispersed in water or an inexpensive organic solvent for application as liquid sprays. These solutions or dispersions may, of course, also be applied as brush applications, as is frequently done in the treatment of the trunks of coffee trees.

Wettable powders can be prepared by grinding together about 20% to 45% by weight of a finely divided carrier such as attapulgite, bentonite, kaolin, diatomaceous earth, or the like, 45% to 80% by weight of the imidazolinyl benzamide, 2% to 5% by weight of a dispersing agent such as the sodium salt of condensed naphthalene sulfonic acids, sodium lignosulfonate, or the like, and 2% to 5% by weight of a surfactant such as sodium N-methyl-N-oleoyl taurate, alkyl phenoxy polyoxyethylene ethanol, or the like.

A typical flowable liquid can be prepared by admixing about 40% by weight of the formula I benzamide with about 2% by weight of gelling clay, 1% by weight of polyethylene glycol, 3% by weight of the sodium salt of condensed naphthalene sulfonic acids and 54% by weight of water.

A typical granular formulation can be prepared by dissolving or dispersing the active ingredient in solvent and applying the solution or dispersion to a sorptive or non-sorptive carrier in sufficient amount to provide 5% to 15% by weight of toxicant on the granular carrier; and a typical emulsifiable concentrate, can be prepared by dissolving about 25% by weight of the formula I imidazolinyl benzamide in 50% by weight of cyclohexanone, 15% by weight of a heavy aromatic solvent such as HiSol, Panasol AN-2, Esso HAN, or the like. While the imidazolinyl benzamides of this invention are illustrated by the structure identified as formula (I) above, it should be understood that these compounds may be tautomeric. As such, they could have the structure:

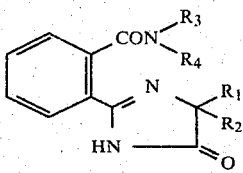

wherein $R_1$, $R_2$, $R_3$ and $R_4$ are as described. Both tautomeric forms are, of course, intended to be included as compounds of the invention when reference is made throughout the specification and claims to the formula I structure.

In accordance with the invention, imidazolinyl benzamides having the structure:

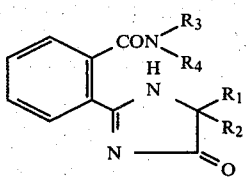

wherein $R_1$, $R_2$, $R_3$ and $R_4$ are as described above, can be prepared by reacting an imidazoisoindoledione having the structure:

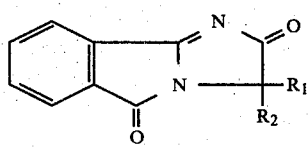

where $R_1$ and $R_2$ are as described above, with an amine represented by the formula: $R_4R_3NH$ (III) where $R_3$ and $R_4$ are as described above.

The mole ratio of amine (II) to imidazoisoindoledione (II) should be in the range of 1:1 to 10:1, and preferably 2:1 to 5:1. The reaction is preferably conducted in a non-protic solvent such as tetrahydrofuran, dioxane, toluene, xylene, benzene, or the like, at a temperature between 50° C. and 100° C.

The reaction may be graphically llustrated as follows:

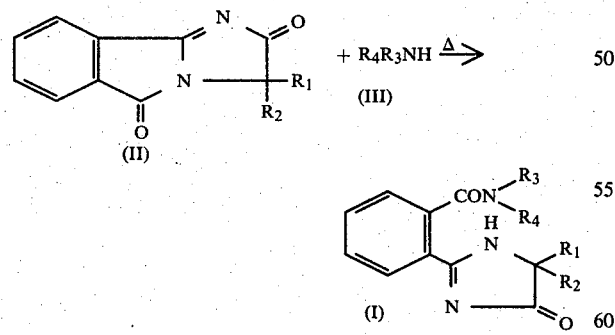

wherein $R_1$, $R_2$, $R_3$ and $R_4$ are as described above.

It should also be understood that when $R_1$ and $R_2$ represent different substituents, the carbon to which $R_1$ and $R_2$ are attached is an asymmetric center and the products (as well as their intermediates) exist in d- and l- forms as well as dl- forms. Further, when the imidazoisoindoledione (II) is optically active and either the d- or l- isomer is reacted with the formula (III) amine, $R_4R_3NH$, the corresponding d- or l-imidazolinyl benzamide (I) is formed.

The intermediate imidazoisoidoledione (II), which are essential to the preparation of the formula (I) imidazolinyl benzamides of the present invention, are described, with a method for their preparation in U.S. Pat. No. 4,017,510, issued Apr. 12, 1977, Ser. No. 631,357, filed Nov. 12, 1975, and incorporated herein by reference thereto.

The invention in the present application is further demonstrated by the examples set forth below.

EXAMPLE 1

Preparation of
o-(5-Isopropyl-5-methyl-4-oxo-2-imidazolin-2-yl)-N,N-dimethylbenzamide.

To a cold solution of 180 g of 3-isopropyl-3-methyl-5$\underline{H}$-imidazo[2,1-a]isoindole-2-(3$\underline{H}$),5-dione in 300 ml of dry tetrahydrofuran in a pressure bottle is added 68 g of dimethylamine. The bottle is sealed and the mixture heated to 50° C. with stirring for 16 hours. The mixture is cooled, and the contents of the bottle transferred to a flask. The solvent is then removed in vacuo. The crystalline residue is then suspended in ether, filtered, washed with ether, and air-dried to give 195 g of o-(5-isopropyl-5-methyl-4-oxo-2-imidazolin-2-yl)-N,N-dimethylbenzamide, melting point 144°–146° C. This product is recrystallized from acetonitrile to give an analytically pure product, melting point 147°–150° C.

EXAMPLE 2

Preparation of Formula I Imidazolinyl Benzamides

Using essentially the same procedure as that described in Example 1, but substituting the appropriate imidazo-[2,1-a]isoindole-2(3$\underline{H}$),5-dione and the appropriate amine for dimethylamine, yields the compounds set forth below.

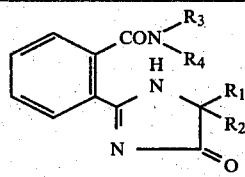

| $R_1$ | $R_2$ | $R_3$ | $R_4$ | Melting Point °C. |
|---|---|---|---|---|
| —(CH$_2$)$_5$— | | H | H | 211–212 |
| CH$_3$ | CH(CH$_3$)$_2$ | H | H | 174–175 |
| CH$_3$ | CH(CH$_3$)$_2$ | H | CH$_3$ | 203–204 |
| —(CH$_2$)$_5$— | | CH$_3$ | CH$_3$ | 189–190.5 |
| —(CH$_2$)$_5$— | | H | CH$_3$ | 259–261 |
| CH$_3$ | CH(CH$_3$)$_2$ | H | —CH$_2$C≡CH | 202–205 |

EXAMPLE 3

Plant Growth Regulating Effect of Test Compounds Applied to the Foliage of Plants.

To evaluate test compounds as plant growth regulating agents effective for reducing the relative stem growth of graminaceous crops, said compounds are dissolved or dispersed in 50/50 aqueous/acetone mixtures and applied to the foliage of seedling barley plants (Larker variety) growing in individual cups approximately 7.5 cm square. A sufficient amount of a spreader-sticker is added to the mixture to provide approximately 0.1% by weight thereof in the mixture. The principal functioning agents of the spreader-sticker used are: alkylarylpolyethoxy ethanol, free and combined fatty acids, glycol ethers (di-alkyl), benzenedicarboxylate and isopropanol. This spreader-sticker has a specific gravity of 0.90 at 20/20° C.; a density of 898.5 g/L at 20° C.; a surface tension of 30 dynes/cm at 0.1% concentration in water; and a pH of 6±0.5 as a liquid spray film. It is marketed as BioFilm ® by Colloidal Products Corporation of Sausolito, Calif.

The treatment consists of spraying the compound in acetone:water (1:1) at the rate of 747 liters per hectare on seedling barley plants, using a moving nozzle which travels along a stationary track above the plants, at a constant speed. In these tests, compound is applied at rates of from 0.056 to 6.72 kg per hectare.

The treated plants are placed on greenhouse benches and watered and fertilized in accordance with normal greenhouse procedures.

Three weeks after treatment, plants are measured, and in some instances harvested and weighed. The height of control plants and treated plants are recorded and reported in Table I below.

TABLE I

Evaluation of Test Compounds for Reducing the Relative Stem Growth of Barley Plants (Larker Variety); Said Compound having the Structure:

| $R_1$ | $R_2$ | $R_3$ | $R_4$ | Rate kg/Hectare | Barley Height cm | Weight gram |
|---|---|---|---|---|---|---|
|  |  | Control |  | — | 11.7 | 16.2 |
| $CH_3$ | $-CH(CH_3)_2$ | $CH_3$ | $CH_3$ | 0.56 | 9.5 | 14.4 |
|  |  |  |  | 0.165 | 9.8 | 15.0 |
|  |  |  |  | 0.056 | 10.8 | 14.2 |
|  |  | Control |  | — | 17.8 | 15.3 |
|  | $-(CH_2)_5-$ | H | $CH_3$ | 6.72 | 16.3 | 16.0 |
|  |  |  |  | 3.36 | 17.8 | 17.2 |
|  |  |  |  | 1.12 | 16.8 | 15.4 |
|  |  | Control |  | — | 33.3 | — |
|  | $-(CH_2)_5-$ | $CH_3$ | $CH_3$ | 2.24 | 32.0 | — |
|  |  |  |  | 0.56 | 32.2 | — |
|  |  |  |  | 0.11 | 33.6 | — |
| $CH_3$ | $-CH(CH_3)_2$ | H | $-CH_2-C\equiv CH$ | 2.24 | Dead | — |
|  |  |  |  | 8.56 | 21.8 | — |
|  |  |  |  | 0.11 | 33.2 | — |

EXAMPLE 4

Evaluation of Imidazolinyl Benzamides for Reducing the Stem Growth of Corn and Snapbeans.

These evaluations are made following the procedure of Example 3, but substituting corn and snapbeans for barley. In these tests, seedling corn and snapbean plants are sprayed with aqueous/acetone (1:1) mixtures having a sufficient amount of test compound dissolved or dispersed therein to provide from 0.056 to 6.72 kg/hectare of test compound per treatment.

The varieties of corn and snapbeans used in these tests are, respectively, Field Corn FR-619 and Greensleeves.

Reduction of stem growth of treated plants is evident from the data obtained in these tests and reported in Table II below.

TABLE II

Evaluation of Test Compounds for Reducing the Relative Stem Growth of Corn and Snapbeans; Said Compound having the Structure:

| $R_1$ | $R_2$ | $R_3$ | $R_4$ | Rate kg/Hectare | Corn Height cm | Weight gram | Snapbeans Height cm | Weight gram |
|---|---|---|---|---|---|---|---|---|
|  |  | Control |  | — | 86.0 | 25.3 | 42.5 | 27.0 |
| $CH_3$ | $-CH(CH_3)_2$ | H | $CH_3$ | 2.24 | 81.0 | 25.4 | 37.0 | 24.4 |
|  |  |  |  | 0.44 | 84.6 | 22.3 | 41.8 | 24.0 |
|  |  |  |  | 0.11 | 76.8 | 19.8 | 41.0 | 22.8 |
| $CH_3$ | $-CH(CH_3)_2$ | $CH_3$ | $CH_3$ | 0.56 | 70.2 | 19.8 | 23.0 | 16.2 |
|  |  |  |  | 0.165 | 80.2 | 21.5 | 30.6 | 20.6 |
|  |  |  |  | 0.056 | 77.8 | 23.2 | 37.8 | 20.2 |
|  |  | Control |  | — | 78.9 | 23.8 | 36.2 | 22.4 |
| $CH_3$ | $-CH(CH_3)_2$ | $CH_3$ | $CH_3$ | 0.56 | 62.8 | 16.7 | 21.6 | 9.3 |
|  |  |  |  | 0.165 | 61.0 | 12.8 | 20.0 | 18.3 |

TABLE II-continued

Evaluation of Test Compounds for Reducing the Relative Stem Growth of Corn and Snapbeans; Said Compound having the Structure:

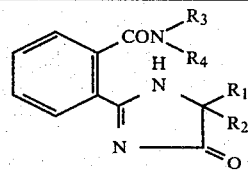

| | | | | | Corn | | Snapbeans | |
|---|---|---|---|---|---|---|---|---|
| $R_1$ | $R_2$ | $R_3$ | $R_4$ | Rate kg/Hectare | Height cm | Weight gram | Height cm | Weight gram |
| Control | | | | 0.056 | 73.0 | 16.8 | 20.6 | 18.3 |
| | | | | — | 77.9 | 33.4 | 35.6 | 21.4 |
| —(CH$_2$)$_5$— | | H | CH$_3$ | 6.72 | 76.0 | 38.6 | 30.6 | 20.8 |
| | | | | 3.36 | 73.4 | 35.6 | 35.4 | 22.5 |
| | | | | 1.12 | 70.8 | 33.0 | 37.4 | 21.8 | production and pod weight, averaged. The data obtained are reported in Table III below.

TABLE III

Evaluation of Imidazolinyl Benzamides for Reducing Relative Stem Growth of Soybeans and Increasing Bean Yield

| | | Soybean Varieties | | | | | | |
|---|---|---|---|---|---|---|---|---|
| | | Fiskeby V | | | Bragg | | | |
| Compound | Rate kg/Hectare | Average Plant Height cm | Average Number Beans per Plant | Average Fresh Weight Beans per Plant grams | Average Fresh Weight per Plant grams | Average Number of Pods per Plant | Average Fresh Weight of Pods per Plant grams | Average Dry Weight of Pods per Plant grams |
| Control | — | 43.2 | 32.8 | 34.9 | — | — | — | — |
| o-(5-Isopropyl- 5-methyl-4-oxo- 2-imidazolin- 2-yl)benzamide | 0.112 | 39.4 | 29.6 | 34.2 | | | | |
| | 0.033 | 38.0 | 34.2 | 34.3 | | | | |
| Control | — | — | — | — | 340.9 | 5.0 | 0.50 | 0.08 |
| 0-(5-Isopropyl- 5-methyl-4-oxo- 2-imidazolin- 2-yl)benzamide | 0.112 | | | | 278.4 | 11.2 | 1.22 | 0.23 |
| | 0.033 | | | | 304.5 | 5.2 | 0.48 | 0.10 |

EXAMPLE 5

Evaluation of Imidazolinyl Benzamides as Plant Growth Regulating Agents for Bean-Producing Legumes In these tests, seedling soybean plants, 21 days old, are sprayed with solutions or dispersions of test compound in 50/50 aqueous/acetone mixtures. Test solutions or dispersions contain sufficient amounts of test compound to provide 0.033 or 0.11 kg/hectare thereof to the plant foliage when the plants are sprayed, as described in Example 1 above.

Test solutions, likewise, contain 0.1% by weight of a spreader-sticker, such as described in Example 3 above.

After spraying, the plants are placed on greenhouse benches and watered and fertilized in accordance with normal greenhouse procedures.

Two months after treatment, the plants are transplanted to individual 18 cm pots and returned to the greenhouse for further development.

Twelve weeks after spraying, the test is terminated. The plants are examined, harvested, weighed, the number and weight of the pods on each plant determined, and the pods dried and weighed again.

In these tests, two varieties of soybeans, Bragg and Fiskeby V, were used. Five plants per treatment were employed and the results, as regards plant height, pod

EXAMPLE 6

Evaluation of Imidazolinyl Benzamides as Tobacco Sucker Control Agents

To determine the effectiveness of test compounds for inhibiting bud growth on tobacco plants, Xanthia tobacco plants growing in 18 cm individual pots are topped. Three days after topping, when buds have developed to 1 to 1.5 cm in length, the topped plants are sprayed with an aqueous/acetone (1:1) solution or dispersion of test compound. The solution or dispersion contains 0.1% by weight of a spreader-sticker, such as described in Example 3, and 20 or 100 mg of test compound in 1000 ml of solution. Each plant is sprayed with 200 ml of solution containing 4 or 20 mg of test compound. Five plants per treatment are employed. After spraying, the plants are placed on greenhouse benches and cared for in accordance with normal greenhouse procedures. Three weeks after treatment, all plants are examined and observations recorded. Untreated plants and plants treated with maleic hydrazide (commercial tobacco desuckering agent) are used as controls.

Data obtained are reported in Table IV below, where it can be seen that 20 mg per plant of test compound provides 78.9% bud inhibition; whereas, the commercial bud inhibitor provides only 64.0% bud inhibition.

TABLE IV

Tobacco Bud Inhibition

| Compound | Rate mg/Plant | Average Bud Growth cm | % Inhibition Tobacco Buds |
|---|---|---|---|
| Untreated Control | — | 28.9 | — |
| Maleic Hydrazide | 2 | 28.9 | 0 |
|  | 4 | 25.0 | 13.5 |
|  | 20 | 10.4 | 64.0 |
| o-(5-Isopropyl-5-methyl-4-oxo-2-imidazolin-2-yl)-N,N-dimethylbenzamide | 4 | 28.1 | 2.8 |
|  | 20 | 6.1 | 78.9 |

I claim:

1. A method for eliminating and/or inhibiting bud growth on tobacco plants comprising, applying to the foliage of topped tobacco plants a bud growth inhibiting amount of the compound o-(5-isopropyl-5-methyl-4-oxo-2-imidazolin-2-yl)-N,N-dimethyl-benzamide.

2. A method according to claim 1, wherein said compound is applied to topped tobacco plants at a rate of from 4 to 150 mg per plant.

* * * * *